(12) United States Patent
Linderoth et al.

(10) Patent No.: US 11,446,315 B2
(45) Date of Patent: Sep. 20, 2022

(54) ENHANCEMENT OF CD47 BLOCKADE THERAPY BY PROTEASOME INHIBITORS

(71) Applicant: PF Argentum IP Holdings LLC, New york, NY (US)

(72) Inventors: Emma Linderoth, Toronto (CA); Natasja Nielsen Viller, Oakville (CA); Robert Adam Uger, Richmond Hill (CA); Penka Slavcheva Slavova-Petrova, Toronto (CA)

(73) Assignee: PF Argentum IP Holdings LLC, New York, NY (US)

( * ) Notice: Subject to any disclaimer, the term of this patent is extended or adjusted under 35 U.S.C. 154(b) by 224 days.

(21) Appl. No.: 16/344,974

(22) PCT Filed: Nov. 1, 2017

(86) PCT No.: PCT/CA2017/051300
§ 371 (c)(1),
(2) Date: Apr. 25, 2019

(87) PCT Pub. No.: WO2018/081897
PCT Pub. Date: May 11, 2018

(65) Prior Publication Data
US 2019/0255082 A1 Aug. 22, 2019

Related U.S. Application Data

(60) Provisional application No. 62/416,936, filed on Nov. 3, 2016.

(51) Int. Cl.
| | |
|---|---|
| *A61K 38/08* | (2019.01) |
| *A61K 38/17* | (2006.01) |
| *A61K 47/68* | (2017.01) |
| *A61K 31/69* | (2006.01) |
| *A61P 35/02* | (2006.01) |
| *A61K 31/5355* | (2006.01) |
| *A61K 38/07* | (2006.01) |
| *C07K 7/06* | (2006.01) |
| *C07K 14/705* | (2006.01) |
| *C07K 16/28* | (2006.01) |
| *A61P 35/00* | (2006.01) |
| *C07F 5/02* | (2006.01) |
| *C07F 5/04* | (2006.01) |
| *C07K 16/00* | (2006.01) |
| *A61K 38/00* | (2006.01) |
| *A61K 38/05* | (2006.01) |

(52) U.S. Cl.
CPC .......... *A61K 31/69* (2013.01); *A61K 31/5355* (2013.01); *A61K 38/005* (2013.01); *A61K 38/07* (2013.01); *A61K 38/08* (2013.01); *A61K 38/17* (2013.01); *A61K 38/177* (2013.01); *A61K 47/68* (2017.08); *A61K 47/6811* (2017.08); *A61P 35/00* (2018.01); *A61P 35/02* (2018.01); *C07F 5/025* (2013.01); *C07F 5/04* (2013.01); *C07K 7/06* (2013.01); *C07K 14/705* (2013.01); *C07K 14/70596* (2013.01); *C07K 16/00* (2013.01); *C07K 16/2803* (2013.01); *A61K 38/00* (2013.01); *A61K 38/05* (2013.01); *C07K 2319/30* (2013.01)

(58) Field of Classification Search
CPC .... A61K 38/08; A61K 38/16; A61K 38/1709; A61K 38/177; A61K 47/6811; A61K 31/166; A61K 38/005; A61K 38/05; C07K 7/06; C07K 2319/30; C07K 2319/32; C07K 2319/70
See application file for complete search history.

(56) References Cited

U.S. PATENT DOCUMENTS

| | | |
|---|---|---|
| 6,913,894 B2 | 7/2005 | Buhring et al. |
| 8,361,736 B2 | 1/2013 | Majeti et al. |
| 8,377,448 B2 | 2/2013 | Smith et al. |
| 8,562,997 B2 | 10/2013 | Jaiswal et al. |
| 9,045,541 B2 | 6/2015 | Eckelman et al. |
| 9,650,441 B2 | 5/2017 | Grosveld et al. |
| 9,845,345 B2 * | 12/2017 | Ring .................... A61P 9/10 |
| 9,969,789 B2 | 5/2018 | Uger et al. |
| 10,905,774 B2 * | 2/2021 | Nam ............... C07K 14/70546 |
| 10,906,954 B2 | 2/2021 | Uger et al. |
| 10,907,209 B2 | 2/2021 | Wang et al. |
| 2010/0239578 A1 | 9/2010 | Danska et al. |

(Continued)

FOREIGN PATENT DOCUMENTS

| | | |
|---|---|---|
| EP | 2282772 B1 | 1/2014 |
| WO | WO-2010/070047 A1 | 6/2010 |

(Continued)

OTHER PUBLICATIONS

Korean Application 10-2016-0090233, filed on Jul. 15, 2016, with attached machine translation. (Year: 2016).*

(Continued)

*Primary Examiner* — Jeffrey E. Russel
(74) *Attorney, Agent, or Firm* — Stephen E. Moyer

(57) ABSTRACT

CD47– disease cells such as cancer cells are treated using a combination of CD47 blockade drug and a proteasome inhibitor. The anti-cancer effect of one drug enhances the anti-cancer effect of the other. Specific combinations include SIRPαFc as CD47 blockade drug, and one of bortezomib, ixazomib and carfilzomib as proteasome inhibitor. These combinations are useful particularly to treat blood cancers including lymphomas, leukemias and myelomas.

29 Claims, 4 Drawing Sheets

Figure 1B:
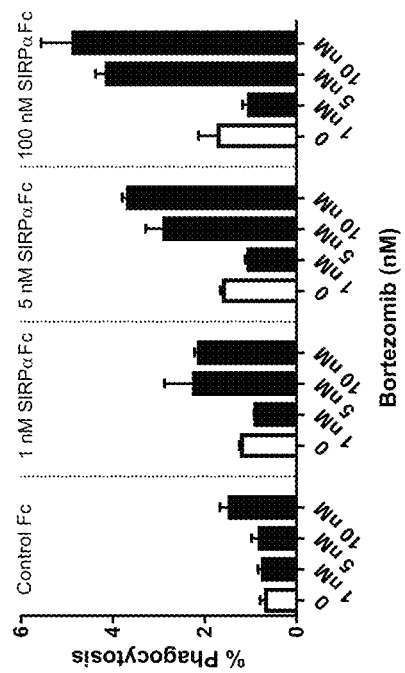

Specification includes a Sequence Listing.

(56) References Cited

U.S. PATENT DOCUMENTS

| | | | |
|---|---|---|---|
| 2010/0239579 | A1 | 9/2010 | Smith et al. |
| 2011/0014119 | A1 | 1/2011 | Jaiswal et al. |
| 2011/0237498 | A1 | 9/2011 | Raymond et al. |
| 2012/0189625 | A1 | 7/2012 | Wang et al. |
| 2013/0011401 | A1 | 1/2013 | Huber et al. |
| 2014/0363442 | A1 | 12/2014 | Frazier et al. |
| 2014/0371247 | A1* | 12/2014 | Colland ............ A61K 45/06 514/266.22 |
| 2017/0224730 | A1* | 8/2017 | Berenson ............ A61K 9/0019 |
| 2018/0312563 | A1 | 11/2018 | Uger et al. |
| 2019/0091290 | A1 | 3/2019 | Lin et al. |
| 2019/0093174 | A1 | 3/2019 | Wang et al. |

FOREIGN PATENT DOCUMENTS

| | | |
|---|---|---|
| WO | WO-2010/083253 A2 | 7/2010 |
| WO | WO-2010/130053 A1 | 11/2010 |
| WO | WO-2011/143624 A2 | 11/2011 |
| WO | WO-2012/083370 A1 | 6/2012 |
| WO | WO-2013/056352 A1 | 4/2013 |
| WO | WO-2013/109752 A1 | 7/2013 |
| WO | WO-2013/119714 A1 | 8/2013 |
| WO | WO-2014/094122 A1 | 6/2014 |
| WO | WO-2014/123580 A1 | 8/2014 |
| WO | WO-2015/021376 A1 | 2/2015 |
| WO | WO-2016/004875 A1 | 1/2016 |
| WO | WO-2016/022971 A1 | 2/2016 |
| WO | WO-2016/023040 A1 | 2/2016 |
| WO | WO-2016/024021 A1 | 2/2016 |
| WO | WO-2016/054555 A2 | 4/2016 |
| WO | WO-2017/177333 A1 | 10/2017 |
| WO | WO-2018012952 A1 * 1/2018 ............ A61P 35/00 |
| WO | WO-2018/081898 A1 | 5/2018 |
| WO | WO-2018/176132 A1 | 10/2018 |
| WO | WO-2018/236904 A1 | 12/2018 |

OTHER PUBLICATIONS

Machine translation of WO 2018/012952 A1, published Jan. 18, 2018. (Year: 2018).*
Allport et al., Endothelial-dependent Mechanisms Regulate Leukocyte Transmigration: A Process Involving the Proteasome and Disruption of the Vascular Endothelial-Cadherin Complex at Endothelial Cell-To-Cell Junctions, J. Exp. Med., 186(4):517-27 (Aug. 1997).
European Patent Application No. 17868118.5, Extended European Search Report, dated Jun. 16, 2020.
Linderoth et al., Abstract 2653: The anti-myeloma activity of TTI-621 (SIRP[alpha]Fc), a CD47-blocking immunotherapeutic, is enhanced when combined with a proteasome inhibitor, Cancer Res., 77(13):2653 (Jul. 2017).
International Application No. PCT/CA2017/051300, International Search Report and Written Opinion, dated Jan. 30, 2018.
Advani et al., The First-In-Class Anti-CD47 Antibody HU5F9-G4 with Rituximab Induces Durable Responses in Relapsed/Refractory DLBCL and Indolent Lymphoma: Interim Phase 1B/2 Results. 24th European Hematology Association Congress. Amsterdam, Netherlands 2019 (Abstract).
Akilov et al., Synergistic Effect of Successive Administration of TTI-621 (SIRPaFc) and PEGylated Interferon-a2a in a Patient with Sezary Syndrome, EORTC CLTF Meeting London 2017.
Chao et al., Anti-CD47 antibody synergizes with rituximab to promote phagocytosis and eradicate non-Hodgkin lymphoma, Cell. 142:669-713 (2010).
Chao et al., The CD47-SIRPa pathway in cancer immune evasion and potential therapeutic implications, Curr. Opin. Immunol. 24:225-32 (2012).
Chow et al., A phase I study of ALX148, a CD47 blocker, in combination with established anticancer antibodies in patients with advanced malignancy. ASCO Annual Meeting. vol. 37. Chicago, IL: American Society of Clinical Oncology; p. 2514 (Abstract) (2019).

Dou et al., Overview of proteasome inhibitor-based anti-cancer therapies: perspective on bortezomib and second generation proteasome inhibitors versus future generation inhibitors of ubiquitin-proteasome system, Curr. Cancer Drug Targets, 14(6):517-36 (2014).
Foon et al., Novel Therapies for Aggressive B-Cell Lymphoma, Adv. Hematol., vol. 2012, Article ID 302570, 22 pages (2012).
Ide et al., Role for CD47-SIRP(Alpha) signaling in xenograft rejection by macrophages, Proceedings of the National Academy of Sciences, National Academy of Sciences. 104:5062-5066 (2007).
Jaiswal et al., CD47 is upregulated on circulating hematopoietic stem cells and leukemia cells to avoid phagocytosis, Cell. 138:271-85 (2009).
Jaiswal et al: Macrophages as mediators of tumor immunosurveillance, Trends Irnmunol 31(6):212-219 (2010).
Kauder et al., ALX148 blocks CD47 and enhances innate and adaptive antitumor immunity with a favorable safety profile, *PLoS One*. 13:e0201832 (2018).
Liu et al., Elimination of tumor by CD47/PD-LI dual-targeting fusion protein that engages innate and adaptive immune responses, *MAbs*. 10:315-324 (2018).
Liu et al., Pre-Clinical Development of a Humanized Anti-CD47 Antibody with Anti-Cancer Therapeutic Potiential, *pLOS One*. 10: e0137345 (2015).
Petrova et al., Lack of CD47 membrane mobility contributes to the poor erythrocyte binding of SIRPaFc, a novel CD47-blocking cancer immunotherapeutic, American Association for Cancer Research, Annual Meeting, Philadelphia, (2015).
Petrova et al., TTI-621 (SIRPaFc): A CD47-Blocking Innate Immune Checkpoint Inhibitor with Broad Antitumor Activity and Minimal Erythrocyte Binding, Clin. Cancer Res., 23(4):1068-1079 (Feb. 2017).
Piccione et al., SIRP(Alpha)-Antibody Fusion Proteins Selectively Bind and Eliminate Dual Antigen-C51 Expressing Tumor Cells, *Clinical Cancer Res*. 22:5109-19 (2016).
Pietsch et al., Anti-leukemic activity and tolerability of anti-human CD47 monoclonal antibodies, *Blood Can. J.* 7:e53G (2017).
Querfeld et al., Intralesional Administration of the CD47 Antagonist TTI-621 (SIRPaFc) Induces Responses in Both Injected and Non-Injected Lesions in Patients with Relapsed/Refractory Mycosis Fungoides and Sezary Syndrome: Interim Results of a Multicenter Phase I Trial, *Blood*. 132(Suppl 1):1653 (2018).
Sallman et al., The first-in-class anti-CD47 antibody Hu5F9-G4 is active and well tolerated alone or with azacitidine in AML and MOS patients: Initial phase 1b results. 2019 ASCO Annual Meeting. vol. 37. Chicago, IL: *J Clin Oncol*. (Abstract) (2019).
Shou, Clinical Proof-of-Concept of an Anti-CD47 Agent for the Treatment of CTCL: Data from Phase 1 Trials of TTI-621 Employing bot Intravenous and Intralesional Routes of Administration. 11th Annual T-Cell Lymphoma Forum. La Jolla, CA (2019).
Sikic et al., First-in-Human, First-in-Class Phase I Trial of the Anti-CD47 Antibody Hu5F9-G4 in Patients With Advanced Cancers, J. Clin. Oncol. 37:946-53 (2019).
Sockolosky, J. T. et al. Durable antitumor responses to CD47 blockade require adaptive immune stimulation, PNAS. 113:E2646-E2654 (2016).
Soto-Pantoja et al., Inhibitory signaling through signal regulatory protein-a is not sufficient to explain the antitumor activities of CD47 antibodies, PNAS, 109(42):E2842-5 (2012).
Tao et al. Targeting CD47 enhances the efficacy of anti-PD-1 and CTLA-4 in an esophageal squamous cell cancer preclinical model. Oncology Research. 25: 579-1587 (2017).
Theocharides et al., Disruption of SIRPa signaling in macrophages eliminates human acute myeloid leukemia stem cells in xenografts, J. Exp. Med., 209(10)1883-1899 (2012).
Trillium expands clinical trial with TTI-621 to include combination with PD-1 blockade [online], Jun. 7, 2017 [retrieved on May 18, 2018 (May 18, 2018)]. Retrieved from: <https://trilliumtherapeutics.com/investors/news/Press-Release-Details/2017/Trillium-Expands-Clinical-Trial-with-TTI-621-to-Include-Combination-with-PD-I-Blockade/default.aspx>.
Uger et al., Cancer immunotherapy targeting CD47: Wild type SIRPaFc is the ideal CD47-blocking agent to minimize unwanted

(56) References Cited

OTHER PUBLICATIONS erythrocyte binding, American Association for Cancer Research, Annual Meeting, San Diego, (2014).

Van et al., CD47(low) status on CD4 effectors is necessary for the contraction/resolution of the immune response in humans and mice, PLoS One. 7:e41972 (2012).

Veillette et al., SIRPa-CD47 Immune Checkpoint Blockade in Anticancer Therapy, Trends Immunol. 39:173-84 (2018).

Weiskopf et al., Engineered SIRPa variants as immunotherapeutic adjuvants to anticancer antibodies, Science. 341:88-91 (2013).

Weiskopf, Cancer immunotherapy targeting the CD47/SIRP(Alpha) axis, Eur. J. Cancer. 76:100-109 (2017).

Willingham et al., Inhibitory signaling through signal regulatory protein-a is not sufficient to explain the antitumor activities of CD47 antibodies, PNAS 109(42):E2842 (2012).

Willingham et al., The CD47-signal regulatory protein alpha (SIRPa) interaction is a therapeutic target for human solid tumor, PNAS, 109(17):6662-6667 (2012).

Yanagita et al., Anti-SIRPa antibodies as a potential new tool for cancer immunotherapy, JCI Insight. 2:e89140 (2017).

Zhao et al., Is targeting of CD47-SIRPa enough for treating hematopoietic malignancy? Blood, 119:4333-4 (2012).

\* cited by examiner

ENHANCEMENT OF CD47 BLOCKADE THERAPY BY PROTEASOME INHIBITORS

This application is a U.S. National Phase of International Patent Application No. PCT/CA2017/051300, filed 1 Nov. 2017, which claims the benefit under 35 USC § 119(e) from U.S. Provisional patent application Ser. No. 62/416,936, filed Nov. 3, 2016, which is incorporated herein by reference in its entirety.

FIELD

The disclosure relates to methods and uses of a drug that blocks the CD47/SIRPα interaction. More particularly, the disclosure relates to methods and means that, in combination, are useful for improving cancer therapy.

BACKGROUND

Cancer cells are targeted for destruction by antibodies that bind to cancer cell antigens, and through recruitment and activation of macrophages by way of Fc receptor binding to the Fc portion of that antibody. Binding between CD47 on cancer cells and SIRPα on macrophages transmits a "don't eat me" signal that enables many tumour cells to escape destruction by macrophages. It has been shown that inhibition of the CD47/SIRPα interaction (CD47 blockade) will allow macrophages to "see" and destroy the target CD47+ cancer cell. The use of SIRPα to treat cancer by CD47 blockade is described in WO2010/130053.

In Applicant's WO2014/094122, a protein drug that inhibits the interaction between CD47 and SIRPα is described. This CD47 blockade drug is a form of human SIRPα that incorporates a particular region of its extracellular domain linked with a particularly useful form of an IgG1-based Fc region. In this form, the SIRPαFc drug shows dramatic effects on the viability of cancer cells that present with a CD47+ phenotype. The effect is seen particularly on acute myelogenous leukemia (AML) cells, and many other types of cancer. A soluble form of SIRPα having significantly altered primary structure and potent CD47 binding affinity is described in WO2013/109752.

Other CD47 blockade drugs have been described, and these include various CD47 antibodies (see for instance Stanford's U.S. Pat. No. 8,562,997, and InhibRx' WO2014/123580), each comprising different antigen binding sites but having, in common, the ability to compete with endogenous SIRPα for binding to CD47, to interact with macrophages and, ultimately, to increase CD47+ disease cell depletion. These CD47 antibodies have activities in vivo that are quite different from those intrinsic to drugs that incorporate SIRPα structure. The latter, for instance, display negligible binding to red blood cells whereas the opposite property seen in CD47 antibodies, and in high affinity SIRPα variants, creates a need for strategies that accommodate a drug "sink" that follows administration.

Still other agents are proposed for use in blocking the CD47/SIRPα axis. These include CD47Fc proteins described in Viral Logic's WO2010/083253, and SIRPα antibodies as described in University Health Network's WO2013/056352, Eberhard's U.S. Pat. No. 6,913,894, and elsewhere.

The CD47 blockade approach in anti-cancer drug development shows great promise. There is a need to provide methods and means for improving the effect of these drugs, and in particular for improving the effect of the CD47 blockade drugs that incorporate SIRPα.

SUMMARY

It is now shown that the anti-cancer effect of a CD47 blockade drug is improved when combined with an agent that inhibits proteasome activity. More particularly, significant improvement in cancer cell depletion is seen when CD47+ cancer cells are treated with a CD47 blockade drug, such as a SIRPα-based drug or a CD47 antibody, in combination with a proteasome inhibitor. The two drugs cooperate and/or synergize in their effects on cancer cells, and result in the depletion of more cancer cells than can be accounted for by their separate, individual effects.

In one aspect, there is provided a method for treating a subject with CD47+ disease cells, comprising administering an effective amount of a drug combination comprising a CD47 blockade drug, such as a CD47-binding form of SIRPα, and a proteasome inhibitor, such as bortezomib, ixazomib and carfilzomib.

In a related aspect, there is provided a use of a CD47 blockade drug, such as a SIRPα-based drug, in combination with a proteasome inhibitor for the treatment of a subject with CD47+ disease cells.

In one embodiment, the CD47 blockade drug can be administered to a subject already treated with a proteasome inhibitor, or the proteasome inhibitor can be administered to a subject already treated with a CD47 blockade drug. The treatment should take advantage of the combined effects of the drug within the recipient.

In another aspect there is provided a combination comprising a CD47 blockade drug and proteasome inhibitor for use in the treatment of CD47+ disease cells.

There is also provided, in another aspect, a kit comprising a combination of a CD47 blockade drug, such as a soluble SIRPα-based drug, and a proteasome inhibitor, together with instructions teaching their use in the treatment of CD47+ disease cells.

In a specific embodiment, the combination of the CD47 blockade drug and proteasome inhibitor is for use in the treatment of cancer.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

These and other aspects of the disclosure are now described in greater detail with reference to the accompanying drawings, in which:

BRIEF REFERENCE TO THE DRAWINGS

Figure 1A:
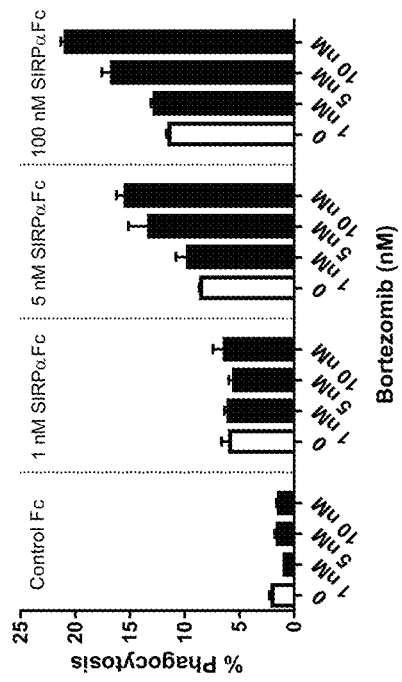

FIGS. 1A and 1B show results when the multiple myeloma cell lines MM1s and H929 are cultured in the presence of the proteasome inhibitor bortezomib (at either 1, 5 or 10 nM) for 48 hours. The 0 result represents phagocytosis of cells that were not treated with bortezomib. Cells are then washed; macrophages and SIRPαFc (at 1, 5 or 100 nM) or Control Fc are added and the mixture is then subjected to the phagocytosis assay described herein. As shown in FIGS.

1A-1B, culturing MM1s (1A) and H929 (1B) in bortezomib for 48 hours results in increased SIRPαFc-mediated phagocytosis.

Figure 2A:
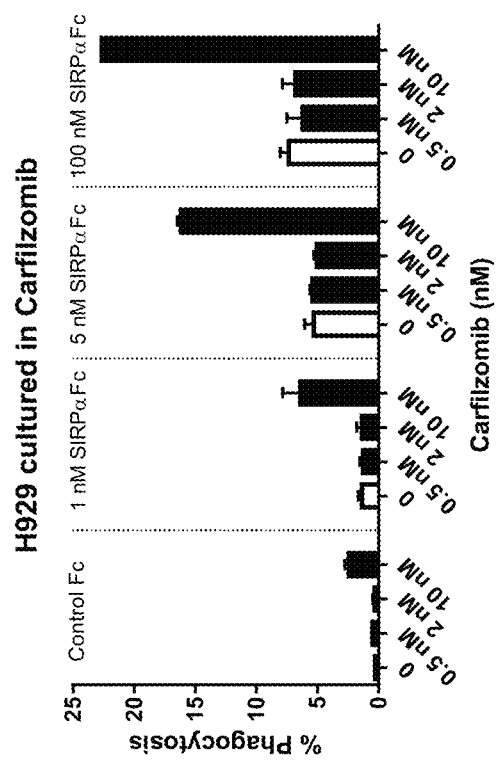
Figure 2B:
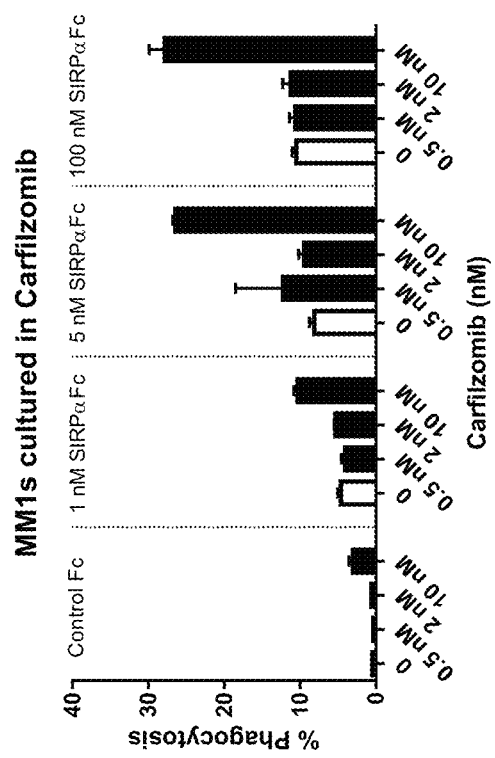
Figure 3A:
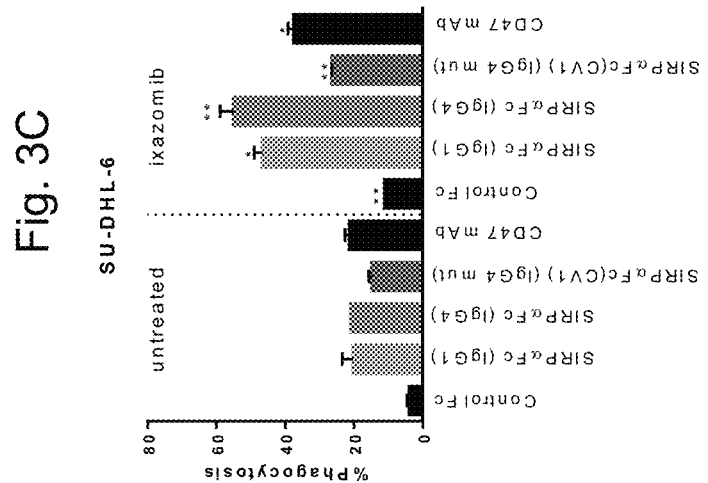
Figure 3B:
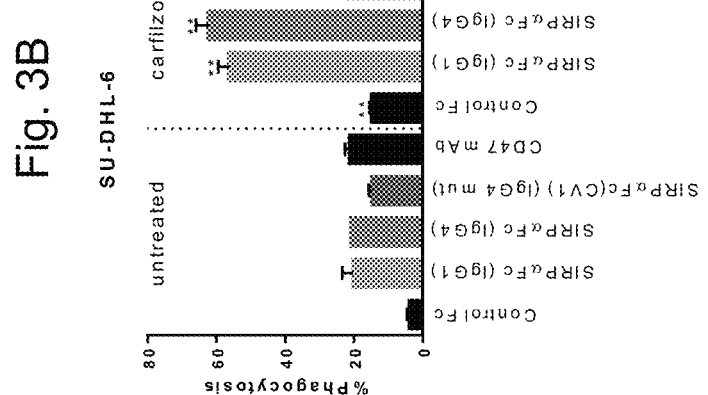
Figure 3C:
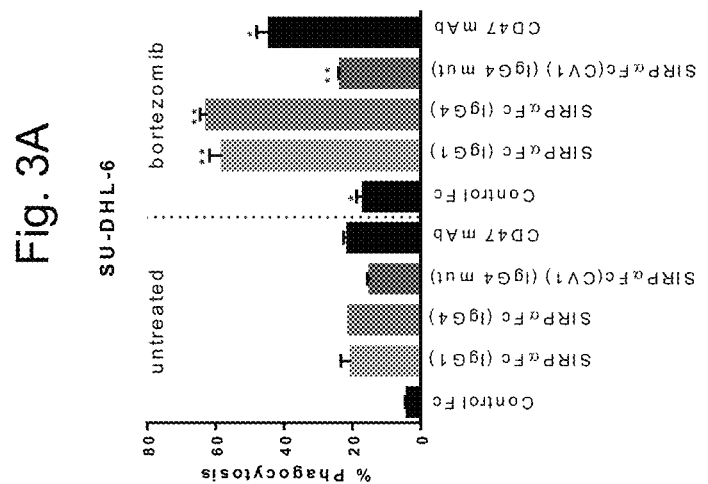
Figure 3D:
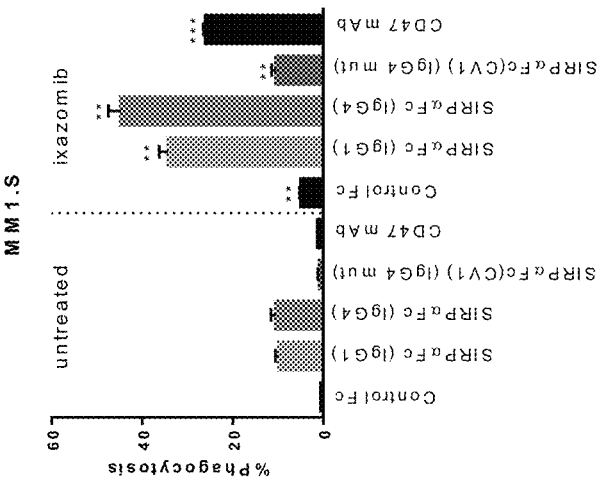
Figure 3E:
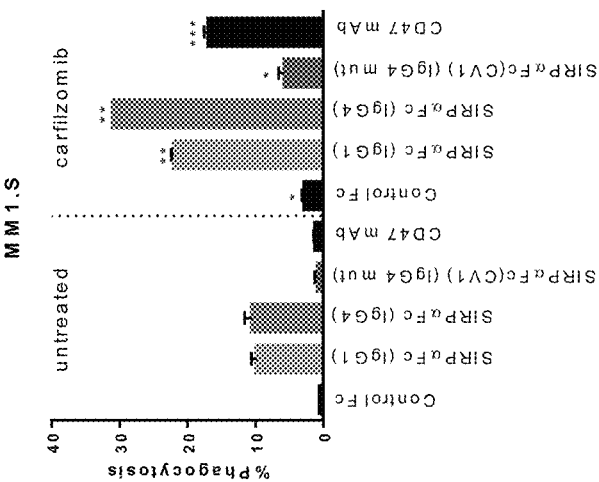
Figure 3F:
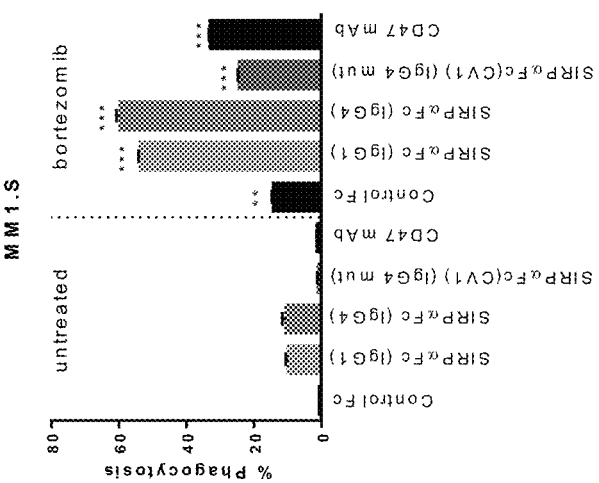

FIGS. 2A and 2B show results from an experiment in which bortezomib is replaced by the proteasome inhibitor carfilzomib, which is then investigated as described in FIGS. 1A-1B. The 0 result represents phagocytosis of cells that were not treated with carfilzomib. Culturing of MM1s (2A) and H929 (2B) in 10 nM carfilzomib resulted in a significant increase in SIRPαFc-mediated phagocytosis, at all concentrations of SIRPαFc tested.

FIGS. 3A-3F show the effect of proteasome inhibition on phagocytosis mediated by CD47 blockade, from an experiment supplemental to that represented in FIGS. 1A-1B and 2A-2B. The diffuse large cell lymphoma (DLBCL) cell line SU-DHL-6 and the multiple myeloma (MM) cell line MM1.S were cultured in the presence or absence of the proteasome inhibitors bortezomib (10 nM), carfilzomib (10 nM) or ixazomib (25 nM) for 48 hours. Cells were thereafter washed; macrophages and SIRPαFc proteins, CD47 monoclonal antibody (CD47 mAb) or Control Fc (at 100 nM) were added, and the mixture was then subjected to the phagocytosis assay as described infra. As shown in FIGS. 3A-3F, culturing SU-DHL-6 and MM1.S cells in bortezomib (10 nM), carfilzomib (10 nM) or ixazomib (25 nM) for 48 hours results in significantly increased SIRPαFc-mediated phagocytosis or CD47 mAb-mediated phagocytosis.

DETAILED DESCRIPTION

The present disclosure provides an improved method, use, combination and kits for treating subjects that present with disease cells that have a CD47+ phenotype. In particular, it is demonstrated herein that the combination of a CD47 blockade drug and a proteasome inhibitor exhibits an effect that is superior to the effects of either agent alone or of both agents in addition. This statistically significant effect, or benefit, results particularly when the CD47 blockade drug is a soluble SIRPα-based agent. The effect is also seen when the CD47 blockade drug is a CD47-binding antibody. The effect is pronounced when the CD47+ disease cells are CD47+ cancer cells and tumours.

In one aspect, there is provided a method for treating a subject with CD47+ disease cells, comprising administering an effective amount of a drug combination comprising a CD47 blockade drug and a proteasome inhibitor.

In a related aspect, there is provided a use of a CD47 blockade drug in combination with a proteasome inhibitor for the treatment of a subject with CD47+ disease cells.

In another aspect, there is provided a combination comprising a CD47 blockade drug and proteasome inhibitor for use in the treatment of a CD47+ disease.

In a further aspect, there is provided a kit comprising a combination comprising a CD47 blockade drug and proteasome inhibitor together with instructions for the use in the treatment of CD47+ disease cells.

There is also provided, in another aspect, a kit comprising a combination of a CD47 blockade drug and a proteasome inhibitor, together with instructions teaching their use in the treatment of CD47+ disease cells.

The term CD47+ disease cells means cells having the phenotype CD47+ and are associated with a disease. Cells that are CD47+ can be identified using the methods disclosed herein. In one embodiment, the CD47+ disease cells are cancer cells.

As used herein, a CD47 blockade drug can be any drug or agent that interferes with and dampens or blocks signal transmission that results when CD47 interacts with macrophage-presented SIRPα. The CD47 blockade drug is an agent that inhibits CD47 interaction with SIRPα. The CD47 blockade drug is preferably an agent that binds CD47 and blocks its interaction with SIRPα. The CD47 blockade drug can be an antibody or antibody-based antagonist of the CD47/SIRPα signaling axis, such as an antibody that binds CD47 and blocks interaction of CD47 with SIRPα. Desirably, but not essentially, the CD47 blockade drug comprises a constant region, i.e., an Fc region, that can be bound by macrophages that are activated to destroy cells to which the CD47 blockade drug is bound, such as cancer cells. The CD47 blockade drug Fc region preferably has effector function, and is derived from either IgG1 or IgG4 including IgG4(S228P). In the alternative, the Fc region can be one that is altered by amino acid substitution to reduce effector function to an inactive state.

CD47-binding forms of human SIRPα are the preferred CD47 blockade drugs for use in the combination herein disclosed. These drugs are based on the extracellular region of human SIRPα. They comprise at least a part of the extracellular region sufficient to confer effective CD47 binding affinity and specificity. So-called "soluble" forms of SIRPα, lacking the membrane anchoring component of SIRPα, are useful and are described in the literature and include those referenced in Novartis' WO 2010/070047, Stanford's WO2013/109752, Merck's WO2016/024021 and Trillium's WO2014/094122.

In a preferred embodiment, the soluble CD47-binding form of SIRPα is an Fc fusion. More particularly, the drug suitably comprises the human SIRPα protein, in a form fused directly, or indirectly, with an antibody constant region, or Fc (fragment crystallisable) Unless otherwise stated, the term "human SIRPα" as used herein refers to a wild type, endogenous, mature form of human SIRPα. In humans, the SIRPα protein is found in two major forms. One form, the variant 1 or V1 form, has the amino acid sequence set out as NCBI RefSeq NP_542970.1 (residues 27-504 constitute the mature form). Another form, the variant 2 or V2 form, differs by 13 amino acids and has the amino acid sequence set out in GenBank as CAA71403.1 (residues 30-504 constitute the mature form). These two forms of SIRPα constitute about 80% of the forms of SIRPα present in humans, and both are embraced herein by the term "human SIRPα". Also embraced by the term "human SIRPα" are the minor forms thereof that are endogenous to humans and have the same property of triggering signal transduction through CD47 upon binding thereto. The present disclosure is directed in some embodiments to the drug combinations that include a CD47 blockade drug that comprises the V region of the V2 form of human SIRPα.

In the present drug combination, useful SIRPαFc fusion proteins comprise at least one, such as only one, of the three so-called immunoglobulin (Ig) domains that lie within the extracellular region of human SIRPα. More particularly, the present SIRPαFc proteins incorporate at least residues 32-137 of human SIRPα (a 106-mer), which constitute and define the IgV domain of the V2 form of human SIRPα, according to current nomenclature. This SIRPα sequence, shown below, is referenced herein as SEQ ID No. 1.

(SEQ ID No. 1)
EELQVIQPDKSVSVAAGESAILHCTVTSLIPVGPIQWFRGAGPARELIYN

QKEGHFPRVTTVSESTKRENMDFSISISNITPADAGTYYCVKFRKGSPDT

EFKSGA

In a preferred embodiment, the SIRPαFc fusion proteins incorporate the IgV domain as defined by SEQ ID No. 1, and additional, flanking residues that can be contiguous within the SIRPα sequence. This preferred form of the IgV domain, represented by residues 31-148 of the V2 form of human SIRPα, is a 118-mer having SEQ ID No. 2 shown below:

(SEQ ID No. 2)
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPS

Desirable SIRPα fusion proteins incorporate an Fc region that preferably also has effector function. Fc refers to "fragment crystallisable" and represents the constant region of an antibody comprised principally of the heavy chain constant region and components within the hinge region. An Fc component "having effector function" is an Fc component having at least some natural or engineered function, such as at least some contribution to antibody-dependent cellular cytotoxicity or some ability to fix complement. Also, the Fc will at least bind to Fc receptors. These properties can be revealed using assays established for this purpose. Functional assays include the standard chromium release assay that detects target cell lysis. By this definition, an Fc region that is wild type IgG1 or IgG4 has effector function, whereas the Fc region of a human IgG4 mutated to alter effector function, such as by incorporation of an alteration series that includes Pro233, Val234, Ala235 and deletion of Gly236 (EU), is considered not to have effector function. In a preferred embodiment, the Fc is based on human antibodies of the IgG1 isotype. The Fc region of these antibodies will be readily identifiable to those skilled in the art. In embodiments, the Fc region includes the lower hinge-CH2-CH3 domains.

In a specific embodiment, the Fc region is based on the amino acid sequence of a human IgG1 set out as P01857 in UniProtKB/Swiss-Prot, residues 104-330, and has the amino acid sequence shown below and referenced herein as SEQ ID No. 3:

(SEQ ID No. 3)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK*

Thus, in embodiments, the Fc region has either a wild type or consensus sequence of an IgG1 constant region. In alternative embodiments, the Fc region incorporated in the fusion protein is derived from any IgG1 antibody having a typical effector-active constant region. The sequences of such Fc regions can correspond, for example, with the Fc regions of any of the following IgG1 sequences (all referenced from GenBank), for example: BAG65283 (residues 242-473), BAC04226.1 (residues 247-478), BAC05014.1 (residues 240-471), CAC20454.1 (residues 99-320), BAC05016.1 (residues 238-469), BAC85350.1 (residues 243-474), BAC85529.1 (residues 244-475), and BAC85429.1 (residues (238-469).

In the alternative, the Fc region can be a wild type or consensus sequence of an IgG2 or IgG3 sequence, examples thereof being shown below: a human IgG2, for example: APPVAGPSVFLFPPKPKDTLMISRTPE-VTCVVVDVSHEDPEVQFNWYVDGVEVHN AKTKPREEQFN-STFRVVSVLTVVHQDWLNGKEYKCKVSNKGLPA-PIEKTISKTKG QPREPQVYTLPPSREEMTKNQVSLT-CLVKGFYPSDISVEWESNGQPENNYKTTPP MLDSDGSFFLYSK-LTVDKSRWQQGNVFSCSVMHEALHNHYTQKSLSL-SPGK (SEQ ID No. 4), as comprised in P01859 of the UniProtKB/Swiss-Prot database; a human IgG3, for example: APELLGGPSVFLFPPKPKDTLMISRTPE-VTCVVVDVSHEDPEVQFKWYVDGVEVH NAKTKPREEQYN-STFRVVSVLTVLHQDWLNGKEYKCKVSNKALPA-PIEKTISKTK GQPREPQVYTLPPSREEMTKNQVSLT-CLVKGFYPSDIAVEWESSGQPENNYNTTPP MLDSDGSFFLYSKLTVDKSRWQQG-NIFSCSVMHEALHNRFTQKSLSLSPGK (SEQ ID No. 5), as comprised in P01860 of the UniProtKB/Swiss-Prot database;

In other embodiments, the Fc region has a sequence of a wild type human IgG4 constant region. In alternative embodiments, the Fc region incorporated in the fusion protein is derived from any IgG4 antibody having a constant region with effector activity that is present but, naturally, is significantly less potent than the IgG1 Fc region. The sequences of such Fc regions can correspond, for example, with the Fc regions of any of the following IgG4 sequences: P01861 (residues 99-327) from UniProtKB/Swiss-Prot and CAC20457.1 (residues 99-327) from GenBank.

In a specific embodiment, the Fc region is based on the amino acid sequence of a human IgG4 set out as P01861 in UniProtKB/Swiss-Prot, residues 99-327, and has the amino acid sequence shown below and referenced herein as SEQ ID No. 6:

(SEQ ID No. 6)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

In embodiments, the Fc region incorporates one or more alterations, usually not more than about 10, e.g., up to 5 such alterations, including amino acid substitutions that affect certain Fc properties. In one specific and preferred embodiment, the Fc region incorporates an alteration at position 228 (EU numbering), in which the serine at this position is substituted by a proline (S228P), thereby to stabilize the disulfide linkage within the Fc dimer. Other alterations within the Fc region can include substitutions that alter glycosylation, such as substitution of Asn297 by glycine or alanine; half-life enhancing alterations such as T252L, T253S, and T256F as taught in U.S. 62/777,375, and many others. Particularly useful are those alterations that enhance Fc properties while remaining silent with respect to conformation, e.g., retaining Fc receptor binding.

In a specific embodiment, and in the case where the Fc component is an IgG4 Fc, the Fc incorporates at least the S228P mutation, and has the amino acid sequence set out below and referenced herein as SEQ ID No. 7:

(SEQ ID No. 7)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

The CD47 blockade drug used in the combination is thus preferably a SIRPα fusion protein useful to inhibit the binding of human SIRPα with human CD47, thereby to inhibit or reduce transmission of the signal mediated via SIRPα-bound CD47. In embodiments, the fusion protein comprises a human SIRPα component and, fused therewith, an Fc component, wherein the SIRPα component comprises or consists of a single IgV domain of human SIRPα V2 and the Fc component is the constant region of a human IgG having effector function.

In one embodiment, the fusion protein comprises a SIRPα component consisting at least of residues 32-137 of the V2 form of wild type human SIRPα, i.e., SEQ ID No. 1. In a preferred embodiment, the SIRPα component consists of residues 31-148 of the V2 form of human SIRPα, i.e., SEQ ID No. 2. In another embodiment, the Fc component is the Fc component of the human IgG1 designated P01857, and in a specific embodiment has the amino acid sequence that incorporates the lower hinge-CH2-CH3 region thereof i.e., SEQ ID No. 3.

In a preferred embodiment, therefore, the SIRPαFc fusion protein is provided and used in a secreted dimeric fusion form, wherein the fusion protein incorporates a SIRPα component having SEQ ID No. 1 and preferably SEQ ID No. 2 and, fused therewith, an Fc region having effector function and having SEQ ID No.3. When the SIRPα component is SEQ ID No. 1, this fusion protein comprises SEQ ID No. 8, shown below:

(SEQ ID No. 8)
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK*

When the SIRPα component is SEQ ID No. 2, this fusion protein comprises SEQ ID No. 9, a preferred CD47 blockade drug species, shown below:

(SEQ ID No. 9)
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

In alternative embodiments, the Fc component of the fusion protein is based on an IgG4, and preferably an IgG4 that incorporates the S228P mutation. In the case where the fusion protein incorporates the preferred SIRPα IgV domain of SEQ ID No. 2, the resulting IgG4-based SIRPα-Fc protein, another preferred CD47 blockade drug species, has SEQ ID No. 10 shown below:

(SEQ ID No. 10)
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

In preferred embodiment, the fusion protein comprises, as the SIRPα IgV domain of the fusion protein, a sequence that is SEQ ID No. 2. The preferred SIRPαFc is SEQ ID No. 9.

The SIRPα sequence incorporated within the CD47 blockade drug can be varied, as described in the literature. That is, useful substitutions within SIRPα include one or more of the following: L4V/I, V6I/L, A21V, V27I/L, I31T/S/F, E47V/L, K53R, E54Q, H56P/R, S66T/G, K68R, V92I, F94V/L, V63I, and/or F103V. In embodiments, these variants can incorporate a set of amino acid substitutions, such as V6I+V27I+I31F+E47V+K53R+E54Q+H56P+S66T+V92I. CD47-binding SIRPα variants of this type can be used either per se or as Fc fusion proteins, such as G4 Fc fusions and other low effector activity Fc regions including mutated G4.

In a embodiments, the CD47 blockade drug is a variant of human SIRPα having higher binding affinity for human CD47 than wild type SIRPα. In a specific embodiment, the variant SIRPα has the sequence shown in SEQ ID No. 11:

(SEQ ID No. 11)
EEELQIIQPDKSVSVAAGESAILHCTITSLFPVGPIQWFRGAGPARVLIY

NQRQGPFPRVTTVSETTKRENMDFSISISNITPADAGTYYCIKFRKGSPD

TEFKSGAGTELSVRAKP

This SIRPα variant comprises the following amino acid substitutions relative to wild type SIRPα: $V^6I+V^{27}I+I^{31}F+E^{47}V+K^{53}R+E^{54}Q+H^{56}P+S^{66}T+V^{92}I$. In a specific embodiment, this variant SIRPα sequence can be fused with a mutated IgG4 Fc region including a $Ser^{228}Pro$ (EU) having virtually no effector function, to yield a CD47 blockade drug having the sequence:

(SEQ ID No. 12)
EEELQIIQPDKSVSVAAGESAILHCTITSLFPVGPIQWFRGAGPARVLIY

NQRQGPFPRVTTVSETTKRENMDFSISISNITPADAGTYYCIKFRKGSPD

TEFKSGAGTELSVRAKPSESKYGPPCPPCPAPPVAGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK*

Still other types of CD47 blockade drugs can be used in the present method and combination, instead of or in addition to the SIRPα-based drugs. These other drugs include particularly anti-CD47 antibodies, which bind to CD47 and antagonize the interaction with SIRPα. By blocking that interaction, and because of the Fc region of the antibody, the effect of the CD47 antibodies can be similar to the effect of the SIRPα-based Fc fusion drugs. Examples of CD47 antibodies are described in the literature such as Chugai's US2008/0107654; Stanford's WO2009/091601; InhibRx WO2013/119714, Celgene's WO2016/109415; and Janssen's WO2016/081423. Because these antibodies bind red blood cells, a dosing regimen that takes this into account has been developed and is described in WO2014/149477. The properties of a useful anti-CD47 antibody include simply the ability to bind to CD47 in a way that ultimately inhibits signaling by SIRPα, i.e., as an antagonist.

In one embodiment, the CD47 blockade drug is an anti-CD47 antibody that is a chimeric, humanized, human or otherwise recombinant, monoclonal or polyclonal antibody based on the sequence of antibody B6H12 known from the literature and including the sequences:

Amino acid sequence of B6H12 heavy chain variable region:

(SEQ ID No. 13)
EVQLVESGGDLVKPGGSLKLSCAASGFTFSGYGMSWVRQTPDKRLEWVAT

ITSGGTYTYYPDSVKGRFTISRDNAKNTLYLQIDSLKSEDTAIYFCARSL

AGNAMDYWGQGTSVTVSS

Amino acid sequence of B6H12 light chain variable region (SEQ ID No. 14)
DIVMTQSPATLSVTPGDRVSLSCRASQTISDYLHWYQQKSHESPRLLIKF

ASQSISGIPSRFSGSGSGSDFTLSINSVEPEDVGVYYCQNGHGFPRTFGG

GTKLEIK

A full sequence for this antibody and the CDR sequences therein, are available from FIG. 1 in US21030142786, the entire contents of which are incorporated herein by reference.

Other CD47 blockade drugs include CD47Fc proteins, as taught by Viral Logic in WO2010/083253 and by Stanford in U.S. Pat. No. 8,377,448), as well as SIRPα antibodies, as described in UHN's WO2013/056352, Stanford's WO2016/022971, Eberhard's U.S. Pat. No. 6,913,894, and elsewhere.

In a SIRPαFc fusion protein, the SIRPα component and the Fc component are fused, either directly or indirectly, to provide a single chain polypeptide that is ultimately produced as a dimer in which the single chain polypeptides are coupled through intrachain disulfide bonds formed within the Fc region. The nature of the fusing region is not critical. The fusion may be direct between the two components, with the SIRP component constituting the N-terminal end of the fusion and the Fc component constituting the C-terminal end. Alternatively, the fusion may be indirect, through a linker comprised of one or more amino acids, desirably genetically encoded amino acids, such as two, three, four, five, six, seven, eight, nine or ten amino acids, or any number of amino acids between 5 and 100 amino acids, such as between 5 and 50, 5 and 30 or 5 and 20 amino acids. A linker may comprise a peptide that is encoded by DNA constituting a restriction site, such as a BamHI, ClaI, EcoRI, HindIII, PstI, SalI and XhoI site and the like.

The linker amino acids typically and desirably have some flexibility to allow the Fc and the SIRP components to adopt their active conformations. Residues that allow for such flexibility typically are Gly, Asn and Ser, so that virtually any combination of these residues (and particularly Gly and Ser) within a linker is likely to provide the desired linking effect. In one example, such a linker is based on the so-called G4S sequence (Gly-Gly-Gly-Gly-Ser) (SEQ ID No. 15) which may repeat as (G4S)n where n is 1, 2, 3 or more, or is based on (Gly)n, (Ser)n, (Ser-Gly)n or (Gly-Ser)n and the like. In another embodiment, the linker is GTELSVRAKPS (SEQ ID No. 16). This sequence constitutes SIRPα sequence that C-terminally flanks the IgV domain (it being understood that this flanking sequence could be considered either a linker or a different form of the IgV domain when coupled with the IgV minimal sequence described above). It is necessary only that the fusing region or linker permits the components to adopt their active conformations, and this can be achieved by any form of linker useful in the art.

As noted, the CD47 blockade drug such as a SIRPαFc fusion is useful to inhibit interaction between SIRPα and CD47, thereby to block signalling across this axis. Stimulation of SIRPα on macrophages by CD47 is known to inhibit macrophage-mediated phagocytosis by deactivating myosin-II and the contractile cytoskeletal activity involved in pulling a target into a macrophage. Activation of this cascade is therefore important for the survival of CD47+ disease cells, and blocking this pathway enables macrophages to eradicate or at least reduce the active CD47+ disease cell population.

The term "CD47+" is used with reference to the phenotype of cells targeted for binding by the present CD47 blockade drug. Cells that are CD47+ can be identified by flow cytometry using CD47 antibody as the affinity ligand. CD47 antibodies that are labeled appropriately are available commercially for this use (for example, the antibody product of clone B6H12 is available from Santa Cruz Biotechnology). The cells examined for CD47 phenotype can include standard tumour biopsy samples including particularly blood samples taken from the subject suspected of harbouring endogenous CD47+ cancer cells. CD47 disease cells of particular interest as targets for therapy with the present drug combinations are those that "over-express" CD47. These CD47+ cells typically are disease cells, and present CD47 at a density on their surface that exceeds the normal CD47 density for a cell of a given type. CD47 overexpression will vary across different cell types, but is meant herein to refer to any CD47 level that is determined, for instance by flow cytometry or by immunostaining or by gene expression analysis or the like, to be greater than the level measurable on a healthy counterpart cell having a CD47 phenotype that is normal for that cell type.

The present drug combination comprises both a CD47 blockade drug that preferably comprises a soluble form of a SIRPα, as just described, and an inhibitor of a proteasome. In a preferred embodiment, the proteasome inhibitor is bortezomib, or carfilzomib, or ixazomib, or an analog thereof including certain fluorinated analogs, as described herein.

The multi-catalytic proteasome is the ubiquitous proteinase found in cells throughout the plant and animal kingdoms that is responsible for the ubiquitin-dependent degradation of intracellular proteins. Thousands of copies are found in all cells, in both the cytoplasm and the nucleus, which constitute up to 3% of all cellular protein content. Proteasomes serve multiple intracellular functions, including the degradation of damaged proteins and the modulation of many regulatory proteins that affect inflammatory processes, viral shedding, the cell cycle, growth, and differentiation.

The ubiquitin-proteasome pathway (UPP), also known as the ubiquitin-proteasome system (UPS), regulates the degradation of intracellular proteins with specificity as to target, time and space. The pathway plays a central role in recognizing and degrading misfolded and abnormal proteins in most mammalian cells. In this pathway, the 26S proteasome is the main proteolytic component, which is found in all eukaryotic cells and is made up of the cylinder-shaped multi-catalytic proteinase complex (MPC) 20S proteasome and two regulatory particles (RP) 19S proteasomes. The 19S proteasome located at each end of the 20S proteasome is made up of 18 subunits, and controls the recognition, unfolding, and translocation of protein substrates into the lumen of the 20S proteasome The 20S proteasome is composed of 28 protein subunits arranged in four stack rings, with each ring made up of seven α- and β-type subunits, following an α1-7β1-7 stoichiometry. The two outer chambers are formed by α subunits, while the central chamber, containing the proteolytic active sites, is made up of β subunits. Three of the 14 β subunits are responsible for the post-glutamyl peptide hydrolysis activity (PGPH, attributed to β1), trypsin-like activity (T-L, β2), and chymotrypsin-like activity (CT-L, β5), respectively, and all these three active subunits hydrolyze the amide bond of protein substrates with the hydrophilic γ-hydroxyl group of the N-terminal threonine (Oγ-Thrl).

Proteasome inhibitors include those agents that inhibit at least one of the activities of a proteasome subunit or a proteasome complex, such as inhibition of an enzymatic activity. Other proteasome inhibitors include those agents the inhibit formation or interaction of active proteasome complexes.

Useful in combination with a CD47 blockade drug is the first-in-class proteasome inhibitor, bortezomib, a potent, selective, and reversible proteasome inhibitor which targets the 26S proteasome complex and inhibits its function. The successful development of bortezomib (Velcade®) for treatment of relapsed/refractory multiple myeloma (MM) and mantle cell lymphoma, has shown proteasome inhibition to be a useful anti-cancer strategy. Bortezomib primarily inhibits chymotryptic activity, without altering tryptic or caspase-like, proteasome activity. It has pleiotropic effects on multiple myeloma biology by targeting a) cell-cycle regulatory proteins; b) the unfolded protein response (UPR) pathway via modulating the transcriptional activity of plasma cell differentiation factor X-box binding protein-1 (XBP-I); c) p53-mediated apoptosis/MDM2; d) DNA repair mechanisms; and e) classical stress-response pathways via both intrinsic (caspase-9 mediated) and extrinsic (caspase-3 mediated) cell death cascades. Specifically, bortezomib activates c-Jun N-terminal kinase (JNK), which triggers mitochondrial apoptotic signalling: release of cytochrome-c (cyto-c) and second mitochondrial activator of caspases (Smac) from mitochondria to cytosol, followed by activation of caspase-9 and caspase-3.

Another proteasome inhibitor useful in the present combination is a structural analogue of the microbial natural product epoxomicin, now known as carfilzomib (also called PR-171). Carfilzomib selectively inhibits the CTL activity of the 20S proteasome with minimal cross reactivity to other proteasome classes.

Clinical studies have demonstrated that consecutive daily dosing schedules with carfilzomib are both well-tolerated and promote antitumor activity in hematologic malignancies, including patients previously treated with bortezomib.

Thus, in the present method, a CD47 blockade drug is used in combination with a proteasome inhibitor, especially bortezomib, ixazomib and carfilzomib. The proteasome inhibitors useful in the present method also include a number and variety of clinically advanced or marketed compounds such as bortezomib sold as Velcade® (PS-341), carfilzomib sold as Kyprolis® (PR 171), ixazomib (MLN-9708/2238), delanzomib (CEP-18770), oprozomib (ONX-0912, PR-047) and marizomib (NPI-0052, salinosporamide A).

Proteasome inhibitors useful in the present method, use and combination thus include, as a class, a variety of boron-containing peptide-based structures, i.e., the peptidic boronic acids that include bortezomib, ixazomib, and delanzomib, and numerous analogs.

Proteasome inhibitors useful in the present method, use and combination also include, as a class, a variety of peptide epoxyketones that include carfilzomib, and oprozomib, and numerous analogs.

Still other proteasome inhibitors useful in the present method, use and combination include lactacystin, disulfiram, expoxomicin, G132, β-hydroxy β-methylbutyrate, epigallocatechin-3-gallate, MLN9708, and CD P-18770.

In a specific embodiment of the present method, use and combination, the CD47 blockade drug is used in combination with bortezomib, having the structure:

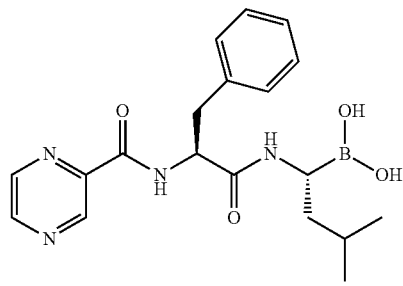 [SMILES: CC(C)C[C@H](NC(=O)[C@H](Cc1ccccc1)NC(=O)c1cnccn1)B(O)O]

As noted, bortezomib is marketed under the trademark Velcade® and is provided as a lyophilized powder for intravenous injection. It is a reversible inhibitor with a β5>β1 inhibition profile. Established dosing is 1.3 mg/m2 with 2 intravenous administrations on days 1, 4, 8 and 11 of a 21 day cycle. It can be used in combination with doxorubicin and dexamethasone, or in combination with thalidomide, melphalan, prednisone, cyclophosphamide and other agents such as etoposide. It can be used in this same manner for purposes of the present disclosure, although cooperation/interaction with the CD47 blockade drug should permit the use of a reduced bortezomib dose or dosing frequency. It is used particularly for the treatment of multiple myeloma, and can be used for this purpose when combined with CD47 blockade drug for treating this type of blood cancer.

Another boron-containing compound useful the present combination is ixazomib, an orally-available proteasome inhibitor sold as Ninlaro® and used currently in combination with lenalidomide and dexamethasone for the treatment of multiple myeloma. It inhibits proteasome subunit beta type-5. It has the following structure (and is the R-enantiomer):

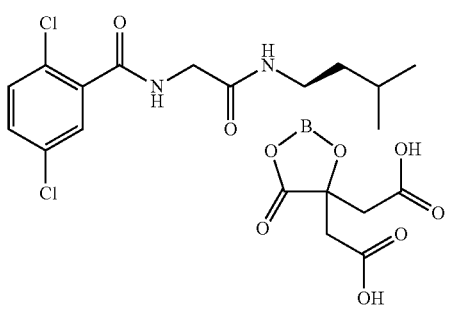

Capsules for oral use contain 4, 3 or 2.3 mg of ixazomib equivalent to 5.7, 4.3 or 3.3 mg of ixazomib citrate, respectively. Inactive ingredients include microcrystalline cellulose, magnesium stearate, and talc.

Another proteasome inhibitor useful in the present combination belongs to the structural family of Formula I shown below:

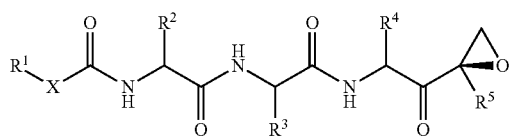

wherein:

$R^1$ is selected from morpholinyl, 1,4-oxazepanyl, thiomorpholinyl, 1,4-thiazepanyl, 1,4-thiazepanyl-1-oxide, 1,4-thiazepanyl-1,1-dioxide, 1,4-thiazinanyl-1-oxide, 1,4-thiazinanyl-1,1-dioxide, aziridinyl, azetidinyl, pyrrolidinyl, piperazinyl, 1,4-diazepanyl, thiazolyl, isothiazolyl, oxazolyl, isooxazolyl, thiophenyl, furanyl, 1,2,4-triazolyl, pyridyl, pyrazinyl, pyrimidinyl and 1,2,4-triazinyl, wherein $R^1$ is optionally substituted with $C_{1-4}$alkyl;

X is absent or $C_{1-4}$alkylene;

$R^2$, $R^3$ and $R^4$ are each independently selected from $C_{1-6}$alkyl, $C_{1-4}$alkylene-phenyl, $C_{1-4}$alkylene-O—$CH_3$, $C_{1-4}$alkylene-O—$CH_2F$, $C_{1-4}$alkylene-O—$CHF_2$ and $C_{1-4}$alkylene-O—$CF_3$, wherein at least one of $R^2$, $R^3$ and $R^4$ is $C_{1-4}$alkylene-O—$CH_2F$, $C_{1-4}$alkylene-O—$CHF_2$ or $C_{1-4}$alkylene-O—$CF_3$; and $R^5$ is $C_{1-6}$alkyl.

In embodiments, a preferred such compound is the following compound:

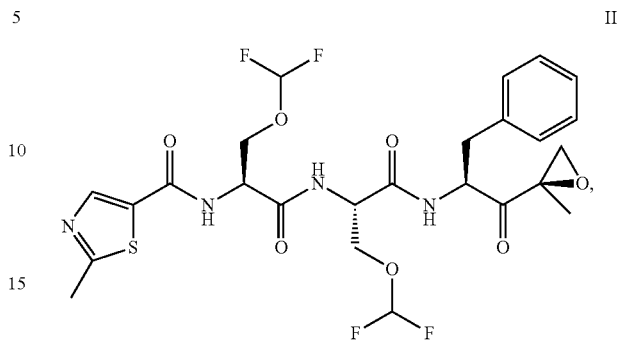

Instead of bortezomib or in addition thereto, the drug combination can include the epoxyketone-based proteasome inhibitor known as carfilzomib having the structure of Formula III shown below:

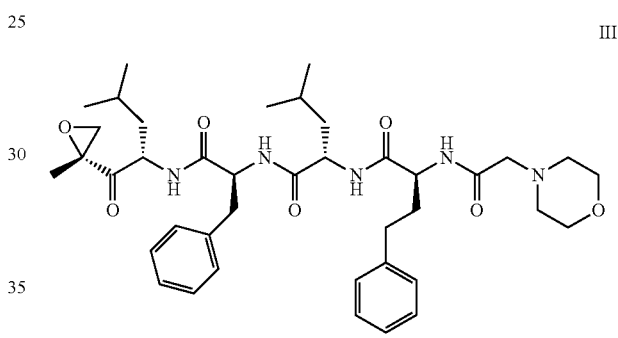

Carfilzomib interferes with the chymotrypsin-like activity of the 20S proteasome that degrades unwanted cellular proteins, causing a build-up of polyubiquinated proteins, which may lead to apoptosis, cycle arrest, and tumor growth inhibition. This tetrapeptide epoxyketone (also an epoxomicin analog) is marketed as Kyprolis® for the treatment of multiple myeloma. In this marketed form, i.e., a form also useful in the present combination, the active ingredient is formulated as monotherapy for a 10-minute infusion and is started at 20 mg/m2 during the first cycle on days 1 and 2. If this dose is tolerated, the dose is increased to 27 mg/m2 for the remaining cycles.

Potent analogs of carfilzomib have more recently been described in WO2014/026282. These fluorinated analogs have the general structure of Formula IV shown below.

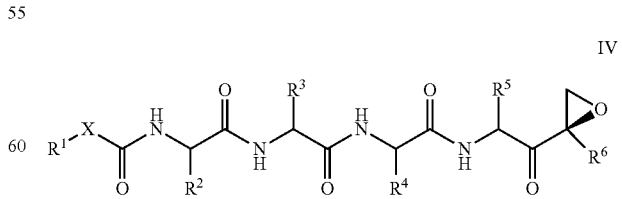

wherein:

$R^1$ is selected from morpholinyl, 1,4-oxazepanyl, thiomorpholinyl, 1,4-thiazepanyl, 1,4-thiazepanyl-1-oxide, 1,4-thiazepanyl-1,1-dioxide, 1,4-thiazinanyl-1-oxide, 1,4-thiazinanyl-1,1-dioxide, aziridinyl, azetidinyl, pyrrolidinyl, piperazinyl and 1,4-diazepanyl;

X is $C_{1-4}$alkylene;

$R^2$, $R^3$, $R^4$ and $R^5$ are each independently selected from the group consisting of $C_{1-6}$alkyl, $C_{1-4}$alkylene-phenyl, $C_{1-4}$alkylene-O—$CH_2F$, $C_{1-4}$alkylene-O—$CHF_2$ and $C_{1-4}$alkylene-O—$CF_3$, wherein at least one of $R^2$, $R^3$, $R^4$ and $R^5$ is $C_{1-4}$alkylene-O—$CH_2F$, $C_{1-4}$alkylene-O—$CHF_2$ or $C_{1-4}$alkylene-O—$CF_3$; and $R^6$ is $C_{1-6}$alkyl.

In embodiments of the present disclosure, the drug combination comprises a species of fluorinated carfilzomib analogs of formula V:

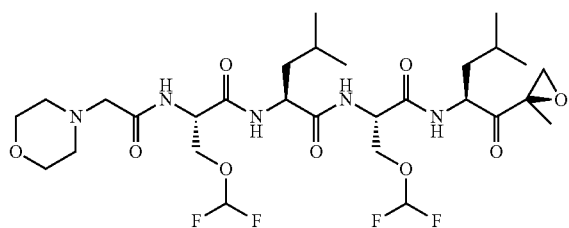

V

Still other CD47 blockade drug combinations can include such proteasome inhibitors as the natural product lactacystin, disulfiram, epigallocatechin-3-gallate, epoxomicin, G132, and β-hydroxy β-methylbutyrate (a proteasome inhibitor in human skeletal muscle). Also, the CD47 blockade drug can be used in combination with a proteasome inhibitor that is an aldehyde (IPSI-001), or a compound that targets ubiquitin E3 ligase such as a cis-imidazoline (nutline-3 and RO5045337 and RO5503781) and a Smac peptide mimetic (LCL161), or an IAP anti-sense termed AEG 35156. The proteasome inhibitor can also be a compound that targets 19S proteasome particularly, such as the quinoline-based ubistatins, and a bis-nitrobenzylidene-piperodinone. Still other compounds useful as proteasome inhibitors include P5091, P22077 as well as WP-1130 which all target DUBs (deubiquitinases).

Each drug included in the combination can be formulated separately for use in combination. The drugs are said to be used "in combination" when, in a recipient of both drugs, the effect of one drug enhances or at least influences the effect of the other drug.

The two drugs in the combination cooperate to provide an effect on target CD47+ cells that is greater than the effect of either drug alone. This benefit manifests as a statistically significant improvement in a given parameter of target cell fitness or vitality. For instance, a benefit in CD47+ cancer cells when a given combination of CD47 blockade drug and proteasome inhibitor is used could be a statistically significant decrease in the number of living cancer cells (hence a depletion), relative to non-treatment, or an increase in the number or size of cancer cells or tumours, or an improvement in the endogenous location or distribution of any particular tumour type. In embodiments, the improvement resulting from treatment with the drug combination can manifest as an effect that is at least additive and desirably synergistic, relative to results obtained when only a single agent is used.

In use, each drug in the combination can be formulated as it would be for monotherapy, in terms of dosage size and form and regimen. In this regard, the synergy resulting from their combined use may permit the use of somewhat reduced dosage sizes or frequencies, as would be revealed in an appropriately controlled clinical trial.

The mechanism by which a proteasome inhibitor contributes to the activity of a CD47 blockade drug, in the present combination, is not known. The proteasome inhibitors likely have a direct activity on some tumour cells, and preliminary data suggest that treatment of tumor cells with proteasome inhibitors results in upregulation of pro-phagocytic ("eat-me") signals such as galectin-3 and galectin-9 on the surface of tumor cells.

In this approach, each drug is provided in a dosage form comprising a pharmaceutically acceptable carrier, and in a therapeutically effective amount. As used herein, "pharmaceutically acceptable carrier" means any and all solvents, dispersion media, coatings, antibacterial and antifungal agents, isotonic and absorption delaying agents, and the like that are physiologically compatible and useful in the art of protein/antibody formulation. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent. Each CD47 blockade drug that is a protein such as SIRPαFc fusion protein and CD47 antibody is formulated using practises standard in the art of therapeutic protein drug formulation. Solutions that are suitable for intravenous administration, such as by injection or infusion, are particularly useful. The inhibitor will of course be formulated as permitted by the regulatory agencies that have approved its use in humans.

Sterile solutions can be prepared by incorporating the active compound in the required amount in an appropriate solvent with one or a combination of ingredients noted above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation are vacuum drying and freeze-drying (lyophilization) that yield a powder of the active ingredient plus any additional desired ingredient from a previously sterile-filtered solution thereof.

As used herein, "effective amount" refers to an amount effective, at dosages and for a particular period of time necessary, to achieve the desired therapeutic result. A therapeutically effective amount of each drug in the combination may vary according to factors such as the disease state, age, sex, and weight of the individual, and the ability of the drug to elicit a desired response in the recipient. A therapeutically effective amount is also one in which any toxic or detrimental effects of the pharmacological agent are outweighed by the therapeutically beneficial effects. The proteasome inhibitor will of course be formulated in amounts that are suitable for patient dosing, as permitted by the regulatory agencies that have approved its use in humans. The CD47 blockade drug can also be administered in amounts that are effective according to clinical trial results. The SIRPαFc having SEQ ID No. 9 can be delivered as a 3 mg dose by intratumoural injection. Some additional guidance can be gleaned from the experimental drug concentrations used with cell-based assays described in the examples herein.

The SIRPαFc fusion protein can be administered to the subject through any of the routes established for protein delivery, in particular intravenous, intradermal and subcutaneous injection or infusion, or by oral or nasal administration.

The drugs in the present combination can be administered sequentially or, essentially at the same time. In embodiments, the proteasome inhibitor can be given before administration of SIRPαFc. In the alternative, the proteasome inhibitor can be given after or during administration of SIRPαFc, or any other CD47 blockade drug alternative. Thus, in embodiments, the subject undergoing therapy is a subject already treated with one of the combination drugs, such as a proteasome inhibitor, that is then treated with the other of the combination drugs, such as a CD47 blockade drug.

Dosing regimens are adjusted to provide the optimum desired response (e.g., a therapeutic response). For example, a single bolus of each drug may be administered, or several divided doses may be administered over time or the dose may be proportionally reduced or increased as indicated by the medical situation. It is especially advantageous to formulate parenteral compositions in unit dosage form for ease of administration and uniformity of dosage. "Unit dosage form" as used herein refers to physically discrete units suited as unitary dosages for the subjects to be treated; each unit contains a predetermined quantity of active compound calculated to produce the desired therapeutic effect in association with the required pharmaceutical carrier.

The drugs can be formulated in combination, so that the combination can be introduced to the recipient in one administration, e.g., one injection or one infusion. Alternatively, and for marketing, the drugs can be combined as separate units that are provided together in a single package, and with instructions for the use thereof according to the present method. In another embodiment, an article of manufacture containing the SIRPαFc drug and proteasome inhibitor combination in an amount useful for the treatment of the disorders described herein is provided. The article of manufacture comprises one or both drugs of the present combination, as well as a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or vial having a stopper pierceable by a hypodermic injection needle). The label on or associated with the container indicates that the composition is to be used so that a recipient receives both the CD47 blockade drug, e.g., a SIRP-based protein, and the proteasome inhibitor in accordance with the present disclosure, thereby to elicit a synergistic effect on the CD47+ disease cells. The article of manufacture may further comprise a second container comprising a pharmaceutically-acceptable buffer, such as phosphate-buffered saline, Ringer's solution and dextrose solution. It may further include other matters desirable from a commercial and use standpoint, including other buffers, diluents, filters, needles, syringes, and package inserts with instructions for use.

For administration the dose for the CD47 blockade drug will be within the range from about 0.0001 to 100 mg/kg, and more usually 0.01 to 5 mg/kg, of the host body weight. For example SIRPαFc dosages can be 0.3 mg/kg body weight, 1 mg/kg body weight, 3 mg/kg body weight, 5 mg/kg body weight or 10 mg/kg body weight or within the range of 0.1-100 mg/kg.

The SIRPαFc protein displays negligible binding to red blood cells. There is accordingly no need to account for an RBC "sink" when dosing with the drug combination. Relative to other CD47 blockade drugs that are bound by RBCs, it is estimated that the present SIRPαFc fusion can be effective at doses that are less than half the doses required for drugs that become RBC-bound, such as CD47 antibodies. Moreover, the SIRPα-Fc fusion protein is a dedicated antagonist of the SIRPα-mediated signal, as it displays negligible CD47 agonism when binding thereto. There is accordingly no need, when establishing medically useful unit dosing regimens, to account for any stimulation induced by the drug.

The drug combination is useful to treat a variety of CD47+ disease cells. These include particularly CD47+ cancer cells, including liquid and solid tumours. Solid tumours can be treated with the present drug combination, to reduce the size, number, distribution or growth rate thereof and to control growth of cancer stem cells. Such solid tumours include CD47+ tumours in bladder, brain, breast, lung, colon, ovary, prostate, liver and other tissues as well. In one embodiment, the drug combination can used to inhibit the growth or proliferation of hematological cancers. As used herein, "hematological cancer" refers to a cancer of the blood, and includes leukemia, lymphoma and myeloma among others. "Leukemia" refers to a cancer of the blood, in which too many white blood cells that are ineffective in fighting infection are made, thus crowding out the other parts that make up the blood, such as platelets and red blood cells. It is understood that cases of leukemia are classified as acute or chronic. Certain forms of leukemia may be, by way of example, acute lymphocytic leukemia (ALL); acute myeloid leukemia (AML); chronic lymphocytic leukemia (CLL); chronic myelogenous leukemia (CML); myeloproliferative disorder/neoplasm (MPDS); and myelodysplastic syndrome. "Lymphoma" may refer to a Hodgkin's lymphoma, both indolent and aggressive non-Hodgkin's lymphoma, cutaneous T cell lymphoma (CTCL), Burkitt's lymphoma, Mantle cell lymphoma (MCL) and follicular lymphoma (small cell and large cell), among others. Myelomas include multiple myeloma (MM), giant cell myeloma, heavy-chain myeloma, and light chain myeloma and Bence-Jones myeloma.

In some embodiments, the hematological cancer treated with the drug combination is a CD47+ leukemia, preferably selected from acute lymphocytic leukemia, acute myeloid leukemia, chronic lymphocytic leukemia, chronic myelogenous leukemia, and myelodysplastic syndrome, preferably, human acute myeloid leukemia.

In other embodiments, the hematological cancer treated with the drug combination is a CD47+ lymphoma or myeloma selected from Hodgkin's lymphoma, both indolent and aggressive non-Hodgkin's lymphoma, diffuse large cell lymphoma (DLBCL), mantle cell lymphoma, T cell lymphoma including mycosis fungoides, Sezary's syndrome, Burkitt's lymphoma, follicular lymphoma (small cell and large cell), multiple myeloma (MM), giant cell myeloma, heavy-chain myeloma, and light chain or Bence-Jones myeloma as well as leimyosarcoma.

In a specific embodiment, the cancer treated with the present combination is multiple myeloma. In another specific embodiment, the targeted cancer is mantle cell lymphoma. In another specific embodiment, the CD47 blockade drug is SIRPαFc. In a further specific embodiment the proteasome inhibitor is bortezomib or carfilzomib or ixazomib.

In still other embodiments, the proteasome inhibitor is bortezomib in combination with SIRPαFc, such as SEQ ID No. 9 or SEQ ID No. 10, such as for the treatment of mantle cell lymphoma, multiple myeloma, or diffuse large cell lymphoma.

Thus, in embodiments, there is provided the use of a CD47 blockade drug in combination with a proteasome inhibitor for the treatment of a particular CD47+ cancer, wherein:

i) the CD47 blockade drug is SIRPαFc of SEQ ID No. 9 and the proteasome inhibitor is bortezomib, such as for the treatment of a cancer that is mantle cell lymphoma or multiple myeloma;
ii) the CD47 blockade drug is SIRPαFc of SEQ ID No. 10 and the proteasome inhibitor is bortezomib, such as for the treatment of a cancer that is mantle cell lymphoma or multiple myeloma;
iii) the CD47 blockade drug is SIRPαFc of SEQ ID No. 9 and the proteasome inhibitor is carfilzomib, such as for multiple myeloma treatment;
iv) the CD47 blockade drug is SIRPαFc of SEQ ID No. 10 and the proteasome inhibitor is carfilzomib, such as for multiple myeloma treatment;
v) the CD47 blockade drug is SIRPαFc of SEQ ID No. 9 and the proteasome inhibitor is ixazomib; such as for multiple myeloma treatment; and
vi) the CD47 blockade drug is SIRPαFc of SEQ ID No. 10 and the proteasome inhibitor is ixazomib, such as for multiple myeloma treatment.

It will be appreciated that other CD47 blockade drugs can be used in combination with other proteasome inhibitors, as discussed supra. Desirable combinations will show a statistically significant improvement in cancer cell response. This can be demonstrated as a statistically significant improvement in proteasome inhibitor activity caused by combination with a CD47 blockade drug, or vice versa, where statistical significance is shown as noted in the examples that follow and desirably, provides a p value>0.05 and more desirably>0.01 such as >0.001.

The combination therapy, comprising CD47 blockade and proteasome inhibition can also be exploited together with any other agent or modality useful in the treatment of the targeted indication, such as surgery as in adjuvant therapy, or with additional chemotherapy as in neoadjuvant therapy.

The following non-limiting examples are illustrative of the present disclosure:

EXAMPLES

To generate the results represented in FIGS. 1A-1B and 2A-2B, heparinized whole blood was obtained from normal healthy human donors (Biological Specialty Corporation) and informed consent was obtained from all donors. Peripheral blood mononuclear cells (PBMCs) were isolated over Ficoll-Paque Plus density gradient (GE Healthcare) and CD14+ monocytes were isolated from PBMCs by positive selection using CD14 antibody-coated MicroBead separation (Miltenyi Biotec). Monocytes were differentiated into macrophages by culturing for seven days in X-Vivo-15 media (Lonza) supplemented with M-CSF (PeproTech). 24 hours prior to the phagocytosis assay, macrophages were primed with IFN-γ (PeproTech). 48 hours prior to the phagocytosis assay, bortezomib (1, 5 or 10 nM) or carfilzomib (0.5, or 2 or 10 nM) were added to tumor cells. On the day of the phagocytosis assay, macrophages were co-cultured with violet proliferation dye 450 (VPD450)-labeled human multiple myeloma cell lines (MM1s or H929) in the presence of 1, 5 or 100 nM human SIRPαFc (V region of human SIRPα variant 2 fused with IgG1 Fc), 100 nM control Fc [human IgG1 Fc region (hinge-CH2-CH3)] for two hours. Phagocytosis was assessed as % VPD450+ cells of live, single CD14+CD11b+macrophages by flow cytometry. Results shown in FIGS. 1A-2B and 2A-2B are representative of two independent experiments.

To generate the results represented in FIGS. 3A-3F, macrophages were prepared from human peripheral blood mononuclear cells (PBMCs) obtained from healthy donors (BioreclamationIVT); informed consent was obtained from all donors. CD14+ monocytes were isolated by positive selection using the EasySep® human monocyte isolation kit (Stemcell Technologies). Monocytes were differentiated into macrophages by culturing the cells in X-VIVO 15 media (Lonza) supplemented with human m-CSF (PeproTech) for 10 days. Macrophages were primed with human IFNγ (PeproTech) one day prior to the phagocytosis assay. 48 hours prior to the phagocytosis assay, bortezomib (10 nM), carfilzomib (10 nM) or ixazomib (25 nM) were added to tumor cells. On the day of the phagocytosis assay, tumor cells (MM1.S or SU-DHL-6) were labeled with Violet Proliferation Dye 450 (BD Biosciences) and cultured with IFNγ-primed macrophages. Macrophages and tumor cells were co-cultured for 2 hours in the presence of 100 nM SIRPαFc (V region of human SIRPα variant 2 fused with IgG1 Fc), SIRPαFc (V region of human SIRPα variant 2 fused with IgG4 Fc), vSIRPαFc (high affinity CV1 variant of V region of human SIRPα fused with mutated IgG4) [SEQ ID No. 12], CD47 monoclonal antibody B6H12 [SEQ ID Nos. 13 and 14] or Control Fc (wild type human IgG4 with stabilized hinge). Cells were subsequently stained with a viability dye, APC-conjugated anti-human CD14 (61D3, eBioscience), and PE-conjugated anti-human CD11b (ICRF44, eBioscience). Macrophages were identified as live, single, CD14+CD11b+ cells. Doublets were excluded by SSC-W and SSC-H discrimination. Percent phagocytosis was assessed as the percent of macrophages that were VPD450+. Unpaired t-tests comparing the percentage of phagocytosis of untreated vs proteasome inhibitor treated tumor cells were performed (*P≤0.05, P≤0.01, *P≤0.001).

Results in FIGS. 3A-3F show that treatment of tumor cells (SU-DHL-6 or MM1.S) with proteasome inhibitors leads to a significant increase in phagocytosis as compared to CD47 blockade alone. The CD47 blockade was achieved by treatment with SIRPαFc (V region of human SIRPα variant 2 fused with IgG1 Fc), SIRPαFc (V region of human SIRPα variant 2 fused with IgG4 Fc), vSIRPαFc (high affinity CV1 variant of V region of human SIRPα fused with mutated IgG4) or CD47 monoclonal antibody (CD47 mAb). In embodiments, the improvement in CD47 blockade drug activity is seen particularly when the CD47 blockade drug is a G1 version of SIRPαFc or a G4 version of SIRPαFc, and the proteasome inhibitor is a peptidic boronate such as bortezomib and ixazomib or a peptidic epoxyketone such as carfilzomib.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A method for treating a subject with CD47+ disease cells comprising administering to the subject a combination of a CD47 blockade drug and a proteasome inhibitor, wherein the CD47 blockade drug comprises a CD47-binding form of human SIRPα, wherein the proteasome inhibitor is an epoxyketone.

2. The method according to claim 1, wherein the proteasome inhibitor is carfilzomib or a fluorinated carfilzomib analog.

3. The method according to claim 1, wherein the CD47-binding form of human SIRPα is a CD47-binding fragment of human SIRPα.

4. The method according to claim 3, wherein the CD47 binding fragment of human SIRPα comprises the V region of human SIRPα.

5. A method for treating a subject with CD47+ disease cells comprising administering to the subject a combination of a CD47 blockade drug and a proteasome inhibitor, wherein the CD47 blockade drug comprises a CD47-binding form of human SIRPα, wherein the CD47 blockade drug is an Fc fusion protein comprising the V region of human SIRPα variant 2.

6. The method according to claim 5, wherein the Fc fusion protein comprises SEQ ID NO: 9 or SEQ ID NO: 10.

7. The method according to claim 1, wherein the CD47 blockade drug comprises soluble human SIRPα having one or more amino acid substitutions selected from $L^4V/I$, $V^6I/L$, $A^{21}V$, $V^{27}I/L$, $I^{31}T/S/F$, $E^{47}V/L$, $K^{53}R$, $E^{54}Q$, $H^{56}P/R$, $S^{66}T/G$, $K^{68}R$, $V^{92}I$, $F^{94}V/L$, $V^{63}I$, and $F^{103}V$.

8. The method according to claim 1, wherein the CD47+ cells are cancer cells.

9. The method according to claim 8, wherein the cancer cells are cells of a cancer type selected from acute lymphocytic leukemia (ALL); acute myeloid leukemia (AML); chronic lymphocytic leukemia (CLL); chronic myelogenous leukemia (CML); myeloproliferative disorder/neoplasm (MPDS); and myelodysplastic syndrome or wherein the cancer is selected from Hodgkin's lymphoma, mantle cell lymphoma, T cell lymphoma, Sezary's syndrome, mycosis fungoides, both indolent and aggressive non-Hodgkin's lymphoma, Burkitt's lymphoma, and follicular lymphoma.

10. The method according to claim 8, wherein the cancer is selected from multiple myeloma (MM), giant cell myeloma, heavy-chain myeloma, and light chain or Bence-Jones myeloma.

11. A method for treating a subject with CD47+ cancer cells, said subject receiving treatment with a proteasome inhibitor, the method comprising administering to the subject a CD47 blockade drug, wherein the CD47 blockade drug comprises a CD47-binding form of human SIRPα, and the amount of the CD47 blockade drug is effective to enhance the anti-cancer effect of the proteasome inhibitor wherein the CD47-binding form of human SIRPα comprises a polypeptide comprising the V region of human SIRPα variant 2, and wherein the CD47 blockade drug comprises the polypeptide comprising the V region of human SIRPα variant 2 fused to a polypeptide comprising an immunoglobulin constant region (Fc) wherein the CD47 blockade drug comprises the amino acid sequence of SEQ ID NO: 9 or SEQ ID NO: 10.

12. A combination comprising an amount of a CD47 blockade drug and an amount of a proteasome inhibitor, wherein the CD47 blockade drug comprises a CD47-binding form of human SIRPα, and wherein the amounts are such that the anti-cancer effects of one of the CD47 blockade drug and the proteasome inhibitor is effective to enhance the anti-cancer effect of the other wherein the CD47-binding form of human SIRPα comprises a polypeptide comprising the V region of human SIRPα variant 2, and wherein the CD47 blockade drug comprises the polypeptide comprising the V region of human SIRPα variant 2 fused to a polypeptide comprising an immunoglobulin constant region (Fc).

13. A kit comprising a combination of claim 12 together with instructions for the use thereof to treat CD47+ disease cells.

14. The method according to claim 8, wherein the CD47 blockade drug and the proteasome inhibitor are administered in amounts effective to exhibit an anti-cancer effect superior to the effects of either agent alone.

15. The method according to claim 8, wherein the CD47 blockade drug and the proteasome inhibitor are administered in amounts effective to exhibit an anti-cancer effect superior to the additive effects of the CD47 blockade drug and the proteasome inhibitor as monotherapy drugs.

16. The method according to claim 10, wherein the CD47 blockade drug and the proteasome inhibitor are administered in amounts effective to exhibit an anti-cancer effect superior to the effects of either agent alone.

17. The method according to claim 10, wherein the CD47 blockade drug and the proteasome inhibitor are administered in amounts effective to exhibit an anti-cancer effect superior to the additive effects of the CD47 blockade drug and the proteasome inhibitor as monotherapy drugs.

18. The combination according to claim 12, wherein the CD47 blockade drug and the proteasome inhibitor are present in the combination in amounts that synergize their effects on cancer cells.

19. The method according to claim 6, wherein the Fc fusion protein comprises SEQ ID NO: 9.

20. The method according to claim 6, wherein the Fc fusion protein comprises SEQ ID NO: 10.

21. The method according to claim 8, wherein the CD47+ cancer cells are leukemia cells.

22. The method according to claim 8, wherein the CD47+ cancer cells are lymphoma cells.

23. The method according to claim 8, wherein the CD47+ cancer cells are myeloma cells.

24. The method according to claim 8, wherein the CD47+ cancer cells are multiple myeloma cells.

25. A method for treating a subject, said subject having CD47+ cancer cells and receiving treatment with a CD47 blockade drug, wherein the CD47 blockade drug comprises a CD47-binding form of human SIRPα, the method comprising administering to the subject a proteasome inhibitor in an amount effective to enhance the anti-cancer effect of the CD47 blockade drug, wherein the CD47-binding form of human SIRPα comprises a polypeptide comprising the V region of human SIRPα variant 2, and wherein the CD47 blockade drug comprises the polypeptide comprising the V region of human SIRPα variant 2 fused to a polypeptide comprising an immunoglobulin constant region (Fc).

26. The method according to claim 25, wherein the CD47 blockade drug comprises the amino acid sequence of SEQ ID NO: 9.

27. The method according to claim 25, wherein the CD47 blockade drug comprises the amino acid sequence of SEQ ID NO: 10.

28. The combination according to claim 12, wherein the CD47 blockade drug comprises the amino acid sequence of SEQ ID NO: 9.

29. The combination according to claim 12, wherein the CD47 blockade drug comprises the amino acid sequence of SEQ ID NO: 10.

* * * * *

SEQUENCE LISTING

<160> NUMBER OF SEQ ID NOS: 16

<210> SEQ ID NO 1
<211> LENGTH: 106
<212> TYPE: PRT
<213> ORGANISM: Homo sapiens

<400> SEQUENCE: 1

Glu Glu Leu Gln Val Ile Gln Pro Asp Lys Ser Val Ser Val Ala Ala
1               5                   10                  15

Gly Glu Ser Ala Ile Leu His Cys Thr Val Thr Ser Leu Ile Pro Val
            20                  25                  30

Gly Pro Ile Gln Trp Phe Arg Gly Ala Gly Pro Ala Arg Glu Leu Ile
        35                  40                  45

Tyr Asn Gln Lys Glu Gly His Phe Pro Arg Val Thr Thr Val Ser Glu
    50                  55                  60

Ser Thr Lys Arg Glu Asn Met Asp Phe Ser Ile Ser Ile Ser Asn Ile
65                  70                  75                  80

Thr Pro Ala Asp Ala Gly Thr Tyr Tyr Cys Val Lys Phe Arg Lys Gly
                85                  90                  95

Ser Pro Asp Thr Glu Phe Lys Ser Gly Ala
            100                 105

<210> SEQ ID NO 2
<211> LENGTH: 118
<212> TYPE: PRT
<213> ORGANISM: Homo sapiens

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 3
<211> LENGTH: 227
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

```
Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 4
<211> LENGTH: 216
<212> TYPE: PRT
<213> ORGANISM: Homo sapiens

<400> SEQUENCE: 4

Ala Pro Pro Val Ala Gly Pro Ser Val Phe Leu Phe Pro Pro Lys Pro
  1               5                  10                  15

Lys Asp Thr Leu Met Ile Ser Arg Thr Pro Glu Val Thr Cys Val Val
             20                  25                  30

Val Asp Val Ser His Glu Asp Pro Glu Val Gln Phe Asn Trp Tyr Val
         35                  40                  45

Asp Gly Val Glu Val His Asn Ala Lys Thr Lys Pro Arg Glu Glu Gln
 50                  55                  60

Phe Asn Ser Thr Phe Arg Val Val Ser Val Leu Thr Val Val His Gln
 65                  70                  75                  80

Asp Trp Leu Asn Gly Lys Glu Tyr Lys Cys Lys Val Ser Asn Lys Gly
                 85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
```

```
                180                 185                 190
Ser Cys Ser Val Met His Glu Ala Leu His Asn His Tyr Thr Gln Lys
            195                 200                 205

Ser Leu Ser Leu Ser Pro Gly Lys
            210                 215

<210> SEQ ID NO 5
<211> LENGTH: 217
<212> TYPE: PRT
<213> ORGANISM: Homo sapiens

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 6
<211> LENGTH: 229
<212> TYPE: PRT
<213> ORGANISM: Homo sapiens

<400> SEQUENCE: 6

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
```

```
            65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
                100                 105                 110
Ser Ile Glu Lys Thr Ile Ser Lys Ala Lys Gly Gln Pro Arg Glu Pro
                115                 120                 125
Gln Val Tyr Thr Leu Pro Pro Ser Gln Glu Glu Met Thr Lys Asn Gln
        130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
                180                 185                 190
Thr Val Asp Lys Ser Arg Trp Gln Glu Gly Asn Val Phe Ser Cys Ser
                195                 200                 205
Val Met His Glu Ala Leu His Asn His Tyr Thr Gln Lys Ser Leu Ser
        210                 215                 220
Leu Ser Leu Gly Lys
225

<210> SEQ ID NO 7
<211> LENGTH: 229
<212> TYPE: PRT
<213> ORGANISM: Homo sapiens

<400> SEQUENCE: 7

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
                20                  25                  30
Leu Met Ile Ser Arg Thr Pro Glu Val Thr Cys Val Val Val Asp Val
                35                  40                  45
Ser Gln Glu Asp Pro Glu Val Gln Phe Asn Trp Tyr Val Asp Gly Val
        50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
                100                 105                 110
Ser Ile Glu Lys Thr Ile Ser Lys Ala Lys Gly Gln Pro Arg Glu Pro
                115                 120                 125
Gln Val Tyr Thr Leu Pro Pro Ser Gln Glu Glu Met Thr Lys Asn Gln
        130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
                180                 185                 190
Thr Val Asp Lys Ser Arg Trp Gln Glu Gly Asn Val Phe Ser Cys Ser
                195                 200                 205
```

```
Val Met His Glu Ala Leu His Asn His Tyr Thr Gln Lys Ser Leu Ser
210                 215                 220

Leu Ser Leu Gly Lys
225

<210> SEQ ID NO 8
<211> LENGTH: 345
<212> TYPE: PRT
<213> ORGANISM: Homo sapiens

<400> SEQUENCE: 8

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345
```

```
<210> SEQ ID NO 9
<211> LENGTH: 345
<212> TYPE: PRT
<213> ORGANISM: Homo sapiens

<400> SEQUENCE: 9

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 10
<211> LENGTH: 347
<212> TYPE: PRT
```

<213> ORGANISM: Homo sapiens

<400> SEQUENCE: 10

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Pro
        115                 120                 125

Cys Pro Ala Pro Glu Phe Leu Gly Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 11
<211> LENGTH: 117
<212> TYPE: PRT
<213> ORGANISM: Homo sapiens

<400> SEQUENCE: 11

Glu Glu Glu Leu Gln Ile Ile Gln Pro Asp Lys Ser Val Ser Val Ala

```
            1               5                  10                 15
          Ala Gly Glu Ser Ala Ile Leu His Cys Thr Ile Thr Ser Leu Phe Pro
                       20                 25                 30

Val Gly Pro Ile Gln Trp Phe Arg Gly Ala Gly Pro Ala Arg Val Leu
                       35                 40                 45

Ile Tyr Asn Gln Arg Gln Gly Pro Phe Pro Arg Val Thr Thr Val Ser
                       50                 55                 60

Glu Thr Thr Lys Arg Glu Asn Met Asp Phe Ser Ile Ser Ile Ser Asn
           65                 70                 75                 80

Ile Thr Pro Ala Asp Ala Gly Thr Tyr Tyr Cys Ile Lys Phe Arg Lys
                           85                 90                 95

Gly Ser Pro Asp Thr Glu Phe Lys Ser Gly Ala Gly Thr Glu Leu Ser
                          100                105                110

Val Arg Ala Lys Pro
                          115

<210> SEQ ID NO 12
<211> LENGTH: 346
<212> TYPE: PRT
<213> ORGANISM: Homo sapiens

<400> SEQUENCE: 12

Glu Glu Glu Leu Gln Ile Ile Gln Pro Asp Lys Ser Val Ser Val Ala
           1               5                  10                 15

Ala Gly Glu Ser Ala Ile Leu His Cys Thr Ile Thr Ser Leu Phe Pro
                           20                 25                 30

Val Gly Pro Ile Gln Trp Phe Arg Gly Ala Gly Pro Ala Arg Val Leu
                           35                 40                 45

Ile Tyr Asn Gln Arg Gln Gly Pro Phe Pro Arg Val Thr Thr Val Ser
                           50                 55                 60

Glu Thr Thr Lys Arg Glu Asn Met Asp Phe Ser Ile Ser Ile Ser Asn
           65                 70                 75                 80

Ile Thr Pro Ala Asp Ala Gly Thr Tyr Tyr Cys Ile Lys Phe Arg Lys
                           85                 90                 95

Gly Ser Pro Asp Thr Glu Phe Lys Ser Gly Ala Gly Thr Glu Leu Ser
                          100                105                110

Val Arg Ala Lys Pro Ser Glu Ser Lys Tyr Gly Pro Pro Cys Pro Pro
                          115                120                125

Cys Pro Ala Pro Pro Val Ala Gly Pro Ser Val Phe Leu Phe Pro Pro
                          130                135                140

Lys Pro Lys Asp Thr Leu Met Ile Ser Arg Thr Pro Glu Val Thr Cys
          145                150                155                160

Val Val Val Asp Val Ser Gln Glu Asp Pro Glu Val Gln Phe Asn Trp
                          165                170                175

Tyr Val Asp Gly Val Glu Val His Asn Ala Lys Thr Lys Pro Arg Glu
                          180                185                190

Glu Gln Phe Asn Ser Thr Tyr Arg Val Val Ser Val Leu Thr Val Leu
                          195                200                205

His Gln Asp Trp Leu Asn Gly Lys Glu Tyr Lys Cys Lys Val Ser Asn
                          210                215                220

Lys Gly Leu Pro Ser Ser Ile Glu Lys Thr Ile Ser Lys Ala Lys Gly
          225                230                235                240

Gln Pro Arg Glu Pro Gln Val Tyr Thr Leu Pro Pro Ser Gln Glu Glu
                          245                250                255
```

```
Met Thr Lys Asn Gln Val Ser Leu Thr Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 13
<211> LENGTH: 118
<212> TYPE: PRT
<213> ORGANISM: Murine

<400> SEQUENCE: 13

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser
        115
```

<210> SEQ ID NO 14
<211> LENGTH: 107
<212> TYPE: PRT
<213> ORGANISM: Murine

<400> SEQUENCE: 14

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys
            100                 105
```

```
<210> SEQ ID NO 15
<211> LENGTH: 5
<212> TYPE: PRT
<213> ORGANISM: Artificial Sequence
<220> FEATURE:
<223> OTHER INFORMATION: Synthetic construct

<400> SEQUENCE: 15

Gly Gly Gly Gly Ser
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic construct

<400> SEQUENCE: 16

Gly Thr Glu Leu Ser Val Arg Ala Lys Pro Ser
1               5                   10
```